(12) United States Patent
Rouster et al.

(10) Patent No.: US 9,404,120 B2
(45) Date of Patent: Aug. 2, 2016

(54) PRODUCTION OF PLANTS HAVING IMPROVED WATER-DEFICIT TOLERANCE

(75) Inventors: Jacques Rouster, Mirefleurs (FR); Christophe Sallaud, Beaumont (FR); Sylvie Coursol, Paris (FR); Michel Zivy, Paris (FR); Laetitia Virlouvet, Epinay-sur-Orge (FR); Claude Welcker, Montferrier-sur-Lez (FR)

(73) Assignee: GENOPLANTS-VALOR, Paris (FR)

( * ) Notice: Subject to any disclaimer, the term of this patent is extended or adjusted under 35 U.S.C. 154(b) by 189 days.

(21) Appl. No.: 13/876,336

(22) PCT Filed: Oct. 14, 2011

(86) PCT No.: PCT/IB2011/054570
§ 371 (c)(1),
(2), (4) Date: Jul. 22, 2013

(87) PCT Pub. No.: WO2012/049663
PCT Pub. Date: Apr. 19, 2012

(65) Prior Publication Data
US 2013/0298282 A1    Nov. 7, 2013

(30) Foreign Application Priority Data

Oct. 15, 2010   (FR) ...................................... 10 04059

(51) Int. Cl.
*C12N 15/82*   (2006.01)
*C07K 14/415*   (2006.01)

(52) U.S. Cl.
CPC .......... *C12N 15/8273* (2013.01); *C07K 14/415* (2013.01)

(58) Field of Classification Search
None
See application file for complete search history.

(56) References Cited

FOREIGN PATENT DOCUMENTS

| WO | 2009/056566 | 5/2009 |
|---|---|---|
| WO | WO 2009/056566 A2 * | 5/2009 |
| WO | 2009/127441 | 10/2009 |

OTHER PUBLICATIONS

Fornalé et al., 2006, Plant Mol. Biol. 62: 809-823.*
Transcription Factor MYB31 [Zea mays], GenBank Accession No. NP_001105949, published Jan. 13, 2008.*
Du et al., 2012, PLoS One 7(6): e37463. Doi:10.1371/journal.pone.0037463.*
Fornalé et al., 2010, Plant Journal 64: 633-644.*
Lewandowska-Gnatowska et al., 2014, Plant Physiology and Biochemistry 82: 202-208.*
He et al. 2011, Cell Research 21: 442-465.*
Weinhold et al., 2013, BMC Plant Biology 13: 99.*

* cited by examiner

*Primary Examiner* — David T Fox
*Assistant Examiner* — Bratislav Stankovic
(74) *Attorney, Agent, or Firm* — Morgan, Lewis & Bockius LLP

(57) ABSTRACT

The present invention relates to a method for increasing the tolerance of a plant to water deficit, which method comprises the overexpression in said plant of an R2R3-MYB subfamily 4 transcription factor.

8 Claims, 1 Drawing Sheet

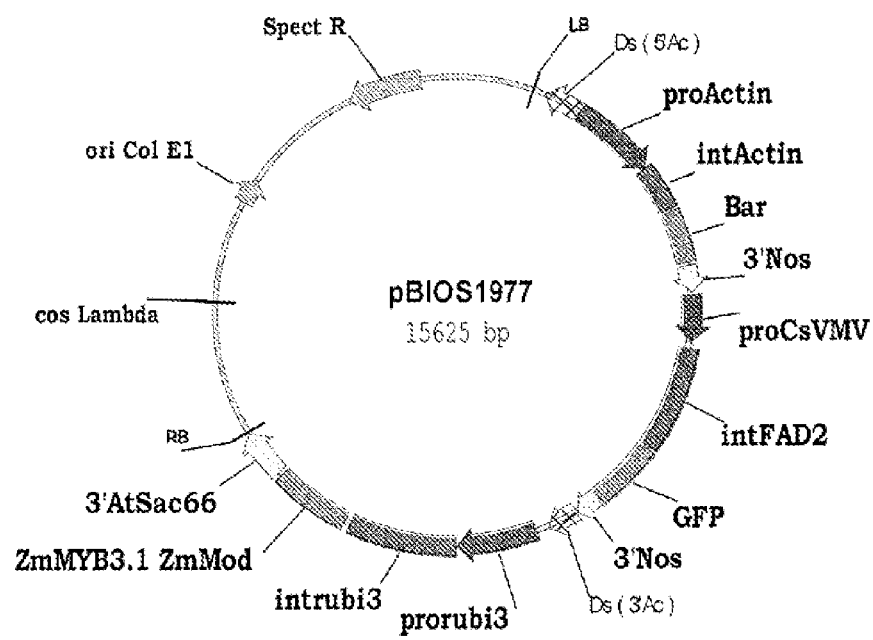
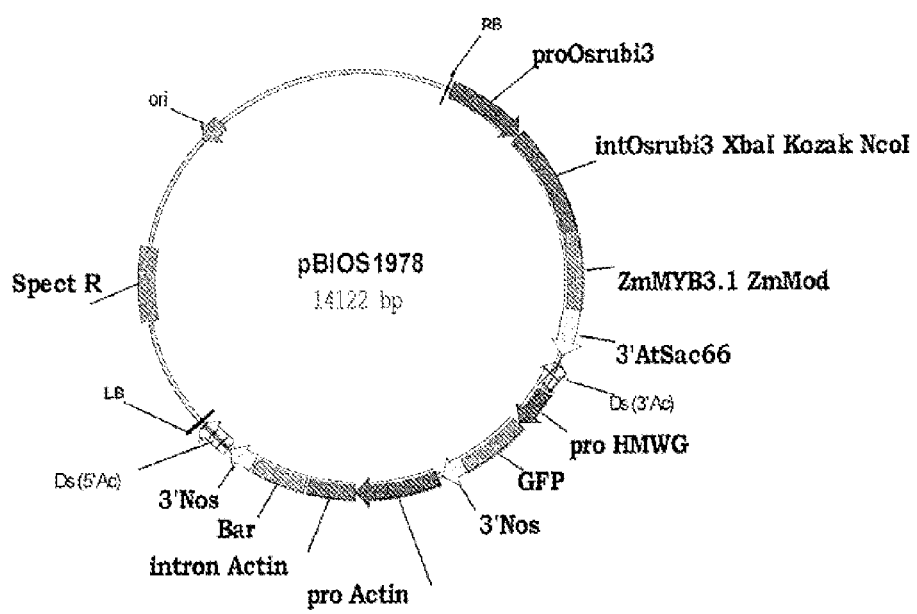

SEQUENCE LISTING

```
<160> NUMBER OF SEQ ID NOS: 5

<210> SEQ ID NO 1
<211> LENGTH: 275
<212> TYPE: PRT
<213> ORGANISM: Zea mays

<400> SEQUENCE: 1

Met Gly Arg Ser Pro Cys Cys Glu Lys Ala His Thr Asn Lys Gly Ala
1               5                   10                  15

Trp Thr Lys Glu Glu Asp Glu Arg Leu Val Ala His Ile Arg Ala His
                20                  25                  30

Gly Glu Gly Cys Trp Arg Ser Leu Pro Lys Ala Ala Gly Leu Leu Arg
            35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Val Lys
65                  70                  75                  80
```

-continued

```
Leu His Ser Val Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Val Thr Glu His His Ala Ser Asn Ile Thr Ile Ser Phe Glu Thr Glu
130                 135                 140

Val Ala Ala Ala Arg Asp Asp Lys Gly Ala Val Phe Arg Leu
145                 150                 155                 160

Glu Asp Glu Glu Glu Glu Arg Asn Lys Ala Thr Met Val Val Gly
                165                 170                 175

Arg Asp Arg Gln Ser Gln Ser His Ser His Ser His Pro Ala Gly Glu
            180                 185                 190

Trp Gly Gln Gly Lys Arg Pro Leu Lys Cys Pro Asp Leu Asn Leu Asp
        195                 200                 205

Leu Cys Ile Ser Pro Pro Cys Gln Glu Glu Glu Met Glu Ala
    210                 215                 220

Ala Met Arg Val Arg Pro Ala Val Lys Arg Glu Ala Gly Leu Cys Phe
225                 230                 235                 240

Gly Cys Ser Leu Gly Leu Pro Arg Thr Ala Asp Cys Lys Cys Ser Ser
                245                 250                 255

Ser Ser Phe Leu Gly Leu Arg Thr Ala Met Leu Asp Phe Arg Ser Leu
            260                 265                 270

Glu Met Lys
        275

<210> SEQ ID NO 2
<211> LENGTH: 53
<212> TYPE: PRT
<213> ORGANISM: Zea mays
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(25)
<223> OTHER INFORMATION: Xaa can be any naturally occurring amino acid
<220> FEATURE:
<221> NAME/KEY: misc_feature
<222> LOCATION: (27)..(45)
<223> OTHER INFORMATION: Xaa can be any naturally occurring amino acid
<220> FEATURE:
<221> NAME/KEY: misc_feature
<222> LOCATION: (47)..(53)
<223> OTHER INFORMATION: Xaa can be any naturally occurring amino acid

<400> SEQUENCE: 2

Xaa Xaa Xaa Xaa Xaa Trp Xaa Xaa Xaa Xaa Xaa Xaa Xaa Xaa Xaa Xaa
1               5                   10                  15

Xaa Xaa Xaa Xaa Xaa Xaa Xaa Xaa Xaa Trp Xaa Xaa Xaa Xaa Xaa Xaa
            20                  25                  30

Xaa Xaa Xaa Xaa Xaa Xaa Xaa Xaa Xaa Xaa Xaa Xaa Xaa Trp Xaa Xaa
        35                  40                  45

Xaa Xaa Xaa Xaa Xaa
    50
```

```
<210> SEQ ID NO 3
<211> LENGTH: 51
<212> TYPE: PRT
<213> ORGANISM: Zea mays
<220> FEATURE:
<221> NAME/KEY: misc_feature
<222> LOCATION: (1)..(24)
<223> OTHER INFORMATION: Xaa can be any naturally occurring amino acid
<220> FEATURE:
<221> NAME/KEY: misc_feature
<222> LOCATION: (26)..(43)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid

<400> SEQUENCE: 3

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Trp Xaa Xaa Xaa Xaa Xaa Xaa Xaa
             20                  25                  30

Xaa Xaa Xaa Xaa Xaa Xaa Xaa Xaa Xaa Xaa Trp Xaa Xaa Xaa Xaa
         35                  40                  45

Xaa Xaa Xaa
     50

<210> SEQ ID NO 4
<211> LENGTH: 5
<212> TYPE: PRT
<213> ORGANISM: Zea mays
<220> FEATURE:
<221> NAME/KEY: VARIANT
<222> LOCATION: (4)..(4)
<223> OTHER INFORMATION: /Replace = Glu

<400> SEQUENCE: 4

Leu Asn Leu Asp Leu
 1               5

<210> SEQ ID NO 5
<211> LENGTH: 828
<212> TYPE: DNA
<213> ORGANISM: Artificial
<220> FEATURE:
<223> OTHER INFORMATION: synthetic sequence encoding ZmMYB31

<400> SEQUENCE: 5
atgggtagaa gtccctgctg cgaaaaggca catactaata aaggagcgtg gacgaaggaa      60
gaggacgaga gactggtggc acatattcgg gcgcacggcg aaggatgctg gcgctccctc     120
cctaaggccg ctggtttgct gcggtgcggc aagtcttgcc gcctccggtg gatcaactac     180
ttgaggccgg acttgaagcg cggtaatttc acggaagagg aggacgagct tatcgtcaag     240
cttcacagtg tcctcggtaa taagtggtct tgatcgccg gcaggctgcc aggtaggact     300
gataacgaga taaagaatta ctggaatacc catatccgca gaaaattgct tagcagaggc     360
atagatcccg tgacgcatag gccagtcaca gaacaccacg cctctaacat caccatctct     420
ttcgagacag aggtggccgc agcggcccgt gatgacaaga agggcgctgt gttccggctt     480
gaggacgagg aggaggaaga gagaaataag gccactatgg tggtgggtcg ggatagacaa     540
tcccagagcc atagccattc gcaccctgct ggtgaatggg gccaaggaaa gcgccctctg     600 aagtgccccgg acctgaacct ggacttgtgt attagcccac cctgccaaga agaggaggag     660
atggaggagg ccgccatgcg tgtcaggcca gctgtgaagc gcgaagcggg cctgtgcttt     720
```

```
ggctgctcgc tcggcctgcc aaggaccgcc gattgcaagt gctccagtag cagcttcctc      780
ggcctgagaa ccgcgatgct cgatttccgg agcctggaga tgaaatag                   828
```

PRODUCTION OF PLANTS HAVING IMPROVED WATER-DEFICIT TOLERANCE

SEQUENCE LISTING SUBMISSION VIA EFS-WEB

A computer readable text file, entitled "045636-5225_SequenceListing.txt," created on or about 26 Mar. 2013, with a file size of about 6 kb contains the sequence listing for this application and is hereby incorporated by reference in its entirety.

The present invention relates to a method for producing plants tolerant to a water deficit.

"Water deficit" corresponds to a situation in which the amount of water transpired by a plant is greater than the amount of water absorbed by said plant.

Water deficit is one of the most important abiotic stresses for plants. It can affect their growth and their reproduction, thus resulting in a loss of yield.

Consequently, it is important to identify genes which have the ability to improve the tolerance of plants to water deficit.

The R2R3-MYB ("myeoblastosis oncogene") transcription factor family has 126 members in *Arabidopsis thaliana* (Stracke et al., Curr. Opin. Plant Biol., 4:447-546, 2001), 84 members in rice (Jiang et al., Genome Bio., 5:R46, 2004) and 192 members in poplar (Wilkins et al., Plant Physiol., 149: 981-993, 2009). This family is characterized by the presence of DNA-binding motifs R2 (of sequence $X_5WX_{19}WX_{19}WX_7$, SEQ ID No. 2) and R3 (of sequence $X_{24}WX_{18}WX_7$, SEQ ID No. 3), which regulate many physiological processes, including control of the cell cycle (Stracke et al., 2001, mentioned above, Fornalé et al., Plant Mol. Biol., 62:809-823, 2006). The alignment of the peptide sequences deduced from the nucleotide sequences encoding these transcription factors has made it possible to classify them in various subfamilies (Stracke et al., 2001, mentioned above). The members of one and the same subfamily—which have similar DNA-binding and protein-protein interaction sites—partially share common biological functions (Jin and Martin, Plant. Mol. Biol., 41:577-585, 1999).

The R2R3-MYB subfamily 4 transcription factors (Fornalé et al., 2006, mentioned above) are generally involved in phenylpropanoid metabolism and lignin biosynthesis (Jin et al., EMBO J., 19:6150-6561, 2000). These transcription factors have, in addition to the two peptide motifs R2 and R3, the peptide motif of sequence LNL[D/E]L (SEQ ID No. 4) in the C-terminal part of the protein (Stracke et al., 2001, mentioned above).

The R2R3-MYB subfamily 4 transcription factors are well known to those skilled in the art. By way of example of R2R3-MYB subfamily 4 transcription factors, mention may be made of those identified by Fornalé et al., 2006 and Wilkins et al., 2009 (mentioned above) and described in Table I hereinafter:

| Species | Protein name | Accession number in the GENBANK or UniProtKB databases | Reference: (a): Fornalé et al., 2006 (b): Wilkins et al., 2009 |
|---|---|---|---|
| Arabidopsis thaliana | AtMYB7 | U26937 | (a) and (b) |
| | AtMYB32 | NM_119665 | |
| | AtMYB4 | AY519615 | |
| | AtY49 | CAA62033 | |
| | AtMYB3 | AF062859 | |
| | AtMYB8 | NP849749 | |
| | AtMYB6 | AL161515 | |
| | AtCAB78069 | CAB78069 | |
| Populus trichocarpa | PtrMYB156 | | (b) |
| | PtrMYB221 | | |
| Populus tremula x Populus tremuloides | PttMYB | CAD98762 | (a) |
| Vitis vinifera | Vv3g1569838 | | (b) |
| | Vv4g15106462 | | |
| Zea mays | ZmMYB38 | P20025 | (a) and (b) |
| | ZmMYB31 | AM156906 | |
| | ZmMYB42 | AM156908 | |
| | ZmMYB8 | AM156905 | |
| Solanum lycopersicum | S1MYB27 (ou LeMYB27) | CAA64614 | (a)and(b) |
| Eucalyptus gunii | EgMYB1 | CAE09058 | (a)and(b) |
| Picea glauca | PgMYB5 | | (b) |
| | PgMYB10 | | |
| | PgMYB13 | | |
| | PgMYB14 | | |
| Tradescantia fluminensis | TfMYB2 | AAS19476 | (a) |
| | TfMYB6 | AAS19480 | |
| | TfMYB1 | AAS19475 | |
| Oryza sativa | OsNP91576 | NP_91576 | (a) |
| | OsT02984 | T02984 | |
| | OsAAV59423 | AAV59423 | |
| | OsPTYPE2 | XP_483665 | |
| | OsPTYPE1 | AAL84628 | |
| Hordeum vulgate | HvMYB5 | CAA50221 | (a)and(b) |
| | HvMYB1 | CAA50224 | |
| Triticum aestivum | TaMYB1 | AAT37167 | (a) |
| Dendrobium sp. | DspMYB8 | AAO49417 | (a) |
| | DspMYB10 | AAO49419 | |
| Gossypium hirsutum | GhMYB9 | AAK19619 | (a) |
| | GhMYB1 | AAN28270 | |
| Antirrhinum majus | AmMYB308 | JQ0960 | (a) |
| | AmMYB330 | JQ0957 | |

Although they belong to the same subfamily, the R2R3-MYB subfamily 4 transcription factors have different functions. Indeed:

tobacco plants transformed with the coding sequence of the *Antirrhinum majus* AmMYB308 or AmMYB330 gene have a phenotype of reduced size and longevity of the leaves exposed to light, the severity of which correlates with the expression level of the transcription factor (Tamagnone et al., Plant Cell, 10:135-154, 1998). However, in these transformed tobacco plants, the overexpression of AmMYB308 results in a repression of the expression of the C4H (cinnamate 4-hydroxylase), 4CL (4-coumarate-CoA ligase), CAD (cinnamyl alcohol dehydrogenase) and CHS (chalcone synthase) genes, but has no effect on the expression of the PAL (phenylalanine ammonia lyase) gene, whereas the overexpression of AmMYB330 also results in a repression of the expression of the 4CL (4-coumarate-CoA ligase) gene, but has no effect on the expression of the CHS gene (contrary to plants overexpressing AmMYB308);

the overexpression of the coding sequence of the AtMYB4 gene in tobacco results in a repression of the expression of the C4H, 4CL and CAD genes. The overexpression of the coding sequence of this AtMYB4 gene in *Arabidopsis thaliana* results in a repression of the expression of the C4H, 4CL1 (4-coumarate-CoA ligase 1) and 4CL3 (4-coumarate-CoA ligase 3) genes, and in induction of the expression of the CCoAOMT (caffeoyl-CoA o-methyltransferase) gene, and has no effect on the expression of the PAL2 (phenylalanine ammonia-lyase 2), F5H (ferulate-5-hydroxylase), COMT (caffeic acid o-methyltransferase) and CAD1 (cinnamyl alcohol dehydrogenase 1) genes (Jin et al., 2000, mentioned above);

the overexpression of the coding sequence of the ZmMYB31 gene in *Arabidopsis thaliana* results in a repression of the expression of the C3H (4-coumarate 3-hydroxylase), 4CL1, F5H and COMT genes, and in induction of the expression of the CHI (chalcone isomerase), F3H (flavone 3-hydroxylase), F3'H (flavonoide 3'-hydroxylase) and DFR (dihydroflavanol reductase) genes and has no effect on the expression of the PAL1 (phenylalanine ammonia-lyase 1), PAL2, C4H, HCT (hydroxycinnamoyl-CoA shikimate/quinate hydroxy-cinnamoyl transferase), 4CL2 (4-coumarate-CoA ligase 2), CCoAOMT, CCR (cinnamoyl-CoA reductase), CAD, Actin, CHS, FLS (flavonol synthase) and UGT73B2 (UDP sugar glycosyltransferase) genes. This overexpression also results in an increase in the H (p-hydroxyphenyl) subunits of lignin in these transgenic plants (Fornalé et al., The Plant Journal, 64, 633-644, 2010);

the overexpression of the coding sequence of the ZmMYB42 gene (the encoded protein of which exhibits 62.1% identity and 70.0% similarity with the peptide sequence of ZmMYB31) in *Arabidopsis thaliana* results in a repression of the expression of the PAL1, C4H, F5H, 4CL1, HCT, COMT, ALDH (aldehyde dehydrogenase), CAD, F3H and F3'H genes, whereas it induces the expression of the CHS gene, and has no effect on the expression of the CHI, FLS, UGTs (UDP sugar glycosyltransferase), SGT (sinapate sinapoyl transferase) and SMT (sinapoyl-glucose malate sinapoyl transferase) genes. This overexpression also results in a decrease in the S (syringyl) subunits of lignin and in an increase in the H (p-hydroxyphenyl) and G (guaiacyl) subunits of lignin in these transgenic plants (Sonbol et al., Plant Mol. Biol., 70:283-96, 2009).

International application WO 01/32002 describes a method for increasing the tolerance of a plant to an abiotic stress (for example drought, temperature, salinity), comprising the modification of the genome of said plant in order to overexpress in said plant an MYB transcription factor chosen from the transcription factors MYB60 (belonging to subfamily 1 according to the subfamily definition given by Stracke et al., 2001, mentioned above), MYB74 (belonging to subfamily 11), MYB75 (belonging to subfamily 6) and MYB90 (also belonging to subfamily 6) of *A. thaliana*.

International application WO 2009/056566 describes a method for increasing yield-related traits (such as biomass) in a plant by modulating the expression in said plant of an MYB7 transcription factor. This increase in the yield-related traits can be carried out under conditions of biotic or abiotic stress. Several corn polypeptide sequences described as being MYB7 transcription factors are disclosed in that document. These "MYB7" transcription factors encompass, in corn, the ZmMYB31 transcription factor (identified as sequence SEQ ID No. 83 in that document) and also several polypeptide sequences having at least 47% identity with the polypeptide sequence of ZmMYB31. However, that document does not show that overexpression of an "MYB7" corn transcription factor in a plant increases the tolerance of a plant to a water deficit. Furthermore, since there are significant functional differences between the various R2R3-MYB transcription factors of one and the same subfamily, it is fairly unlikely that the overexpression, in a plant, of each of the "MYB7" transcription factors described in that document makes it possible to increase yield-related traits whatever the conditions of biotic or abiotic stress, in particular under water deficit conditions.

During their studies, the inventors have demonstrated that transgenic corn (*Zea mays*) plants overexpressing the ZmMYB31 transcription factor exhibit increased tolerance to a water deficit compared with the wild-type (nontransgenic) corn plants. The corn ZmMYB31 transcription factor (available in the GenBank database under accession number GI:89143144; also referenced on the array of the Maize Oligonucleotide Array Project [maizearray.org] under the number MZ00022562) belongs to subfamily 4 of the R2R3-MYB transcription factors. It is also represented by the sequence SEQ ID NO: 1.

Moreover, the inventors have also investigated, in corn (nontransgenic), the candidate genes associated with a corn region located on chromosome 2 and containing a QTL (quantitative trait locus) for sensitivity of leaf growth to edaphic hydric deficit, and also a QTL for protandry under drought conditions (Welcker et al., J Exp Bot., 58, 339-349, 2007). They then identified the gene encoding the R2R3-MYB subfamily 4 transcription factor ZmMYB31 which colocalizes with the targeted region and the relative transcript abundance of which is regulated by the hydric deficit and varies between two subpopulations of recombinant corn lines which differ genetically with respect to the targeted region and heterogeneous on the rest of the genome. Unexpectedly, no other gene encoding an R2R3-MYB subfamily 4 transcription factor, such as those described in Table I above, could be identified by this analysis (combining analysis of gene expression level between two subpopulations of recombinant corn lines which differ genetically with respect to the targeted region and are heterogeneous on the rest of genome, and mapping).

The present invention consequently proposes to use the ZmMY31 protein to increase the resistance of plants to water deficit.

A subject of the present invention is a method for increasing the tolerance of a plant to water deficit, characterized in that an R2R3-MYB subfamily 4 transcription factor, having at least 95% identity and, in increasing order of preference, at least 96%, 97%, 98% and 99% identity, with the sequence SEQ ID No. 1, is overexpressed in said plant.

Unless otherwise specified, the alignment between two peptide sequences and the calculation of the identity percentages are carried out over the entire length of the peptide sequences by means of the "needle" computer program (Needleman and Wunsch, J. Mol. Biol., 48, 443-453, 1970) using the default parameters: "Matrix": EBLOSUM62, "Gap penalty": 10.0 and "Extend penalty": 0.5.

The term "an R2R3-MYB subfamily 4 transcription factor" is intended to mean an R2R3-MYB transcription factor as described by Stracke et al., 2001 (mentioned above), having the conserved DNA-binding motifs R2 (of sequence $X_5WX_{19}WX_{19}WX_7$, SEQ ID No. 2) and R3 (of sequence $X_{24}WX_{18}WX_7$, SEQ ID No. 3), and the conserved motif LNL[E/D]L (SEQ ID No. 4).

According to one advantageous embodiment of the present invention, said R2R3-MYB subfamily 4 transcription factor is derived from a monocotyledonous plant and its peptide sequence comprises the conserved amino acids located at positions 1-9, 11-13, 15-22, 24-25, 27, 30-41, 43-70, 74-75, 77-78, 80-83, 85-93, 95-111, 113-116, 120-127, 138, 140-141, 197, 202-212, 214, 234, 239, 242, 252, 254-255, 261-263, 267-271 and 274-275 of said sequence SEQ ID No. 1 when it is aligned with said sequence SEQ ID No. 1. These conserved amino acids were determined by the inventors by comparing the peptide sequence of the paralogs and orthologs in the monocotyledonous plants *H. vulgare*, *O. sativa* and *T. aestivum*, with the peptide sequence of the ZmMYB31 transcription factor.

The expression "an R2R3-MYB subfamily 4 transcription factor derived from a monocotyledonous plant" is intended to mean an R2R3-MYB subfamily 4 transcription factor expressed by a monocotyledonous plant or a synthetic R2R3-MYB subfamily 4 transcription factor obtained by mutation of an R2R3-MYB subfamily 4 transcription factor expressed by a monocotyledonous plant.

The present invention applies to all monocotyledonous or dicotyledonous plants, and in particular to plants sensitive to water deficit. In a nonlimiting manner, it can apply to edible plants, to ornamental plants, to fruit trees, to large crop plants such as wheat, corn or rice, or to industrial crop plants such as the cotton plant, rape or sunflower, preferably corn.

The overexpression (increase in expression) in a plant of an R2R3-MYB subfamily 4 transcription factor as defined above can be carried out by modification of the genome of the said plant. This modification of the genome can in particular be carried out by genetic transformation of said plant with one or more copies of a polynucleotide encoding said subfamily 4 transcription factor, combined with cis regulatory sequences for its expression. The overexpression of said R2R3-MYB subfamily 4 transcription factor can also be obtained by modification of the cis regulatory sequences for the expression of said R2R3-MYB subfamily transcription factor, for example by replacing its endogenous promoter with a stronger promoter, enabling a higher level of transcription, or else by attaching, to the endogenous promoter, transcription-activating sequences, of "enhancer" type, or translation-activating sequences.

In order to implement the method according to the present invention, use is made of a recombinant expression cassette comprising a polynucleotide encoding an R2R3-MYB subfamily 4 transcription factor as defined above, placed under the transcriptional control of an appropriate promoter.

Said promoter can be a heterologous promoter. In this case, use may be made, for example, of:
- constitutive promoters, such as the endosperm-specific high-molecular-weight glutenin promoter (Verdaguer et al., Plant Mol. Biol., 31:1129-1139, 1996), the CaMV 35S RNA promoter (Odell et al., Nature, 313:810-812, 1985) or the CaMV 19S RNA promoter (Kay et al., Science, 236:1299-1302, 1987), the rice actin 1 promoter (McElroy et al., Plant Cell, 2:163-171, 1990), or the rice or corn ubiquitin 3 promoter (Sivamani and Qu, Plant Mol. Biol., 60:225-239, 2006),
- phloem-specific promoters, such as the Wheat Dwarf Virus promoter (Dinant et al., Physiologia plantarum 121:108-116, 2004; PCT application WO 03/060135) or the AtPP2-A1 promoter (Dinant et al., Plant Physiol., 131: 114-128, 2003),
- leaf-specific promoters, such as the Rubisco small subunit promoter or the phosphoenolpyruvate carboxylase promoter,
- root-specific promoters, such as the rice RCc3 promoter (International application WO 2009/016104) or the rice antiquitin promoter (International application WO 2007/076115), or
- promoters locally inducible by stress (drought, salinity), such as the *Arabidopsis* rd29 promoter (Yamaguchi-Shinozaki and Shinozaki, Mol. Gen. Genet., 236: 331-340, 1993), preferably the endosperm-specific high-molecular-weight glutenin promoter.

It is also possible to use the promoter of an R2R3-MYB transcription factor of a subfamily other than subfamily 4.

To implement the method according to the present invention, use may also be made of recombinant vectors resulting from the insertion of an expression cassette as described above into a host vector.

The expression cassettes and recombinant vectors as described above can, of course, also comprise other sequences, usually employed in constructs of this type. The choice of these other sequences will be made, conventionally by those skilled in the art according to, in particular, criteria such as the host cells selected, the transformation protocols envisioned, etc.

By way of nonlimiting examples, mention will be made of transcription terminators, leader sequences and polyadenylation sites. These sequences can be those which are naturally associated with the gene encoding the R2R3-MYB subfamily 4 transcription factor as defined above, or else can be heterologous sequences. These sequences have no effect on the specific properties of the promoter or of the gene with which they are associated, but can qualitatively or quantitatively improve, overall, transcription and, where appropriate, translation. By way of examples of sequences of this type which are commonly used in plants, mention will be made, among the most widely used, of the CaMV 35S RNA terminator and the nopaline synthase gene terminator. It is also possible, for the purpose of increasing the expression level, to use transcription and translation enhancer sequences.

Among the other sequences commonly employed in the construction of expression cassettes and recombinant vectors mention will also be made of sequences for following the transformation, identification and/or selection of the transformed cells or organisms. These are in particular reporter genes, which confer a readily recognizable phenotype on the transformed cells or organisms, or else selectable marker genes: only the cells or organisms expressing a predetermined selectable marker gene are viable under given conditions (selective conditions). Reporter genes commonly employed are, for example, the beta-glucuronidase (GUS) reporter gene, the luciferase reporter gene or the green fluorescent protein (GFP) reporter gene. Selectable marker genes are generally genes for resistance to an antibiotic, or also, in the case of plants or plant cells, to a herbicide. There is a very large variety of selectable marker genes from which those skilled in the art can choose according to the criteria that they will themselves have determined.

To implement the method according to the present invention, it is also possible to use host cells transformed with a polynucleotide encoding an R2R3-MYB subfamily 4 transcription factor as defined above, which includes in particular host cells transformed with an expression cassette or a recombinant vector as described above.

The term "cell or organism transformed with a polynucleotide" is intended to mean any cell or organism of which the genetic content has been modified by transfer of said polynucleotide into said cell or said organism, whatever the method of transfer that was used, and whether the genetic information provided by said polynucleotide is integrated into the chromosomal DNA or remains extra chromosomal.

The host cells can be prokaryotic or eukaryotic cells. In the case of prokaryotic cells, they can in particular be agrobacteria, such as *Agrobacterium tumefaciens* or *Agrobacterium rhizobium*. In the case of eukaryotic cells, they can in particular be plant cells, derived from monocotyledonous or dicotyledonous plants.

The transgenic plants can be obtained by genetic transformation with at least one polynucleotide, one expression cassette or one recombinant vector as defined above.

Said transgenic plants encompass transgenic monocotyledonous plants, preferably a transgenic corn plant, comprising at least one transgene containing a recombinant expression cassette comprising a polynucleotide encoding an R2R3-MYB subfamily 4 transcription factor as defined above.

A transgenic plant is defined here as a transformed plant in which the exogenous genetic information provided by a transforming polynucleotide is stably integrated into the chromosomal DNA, in the form of a transgene, and can thus be transmitted to the progeny of said plant. This definition therefore also encompasses the progeny of the plants resulting from the initial transgenesis, provided that they contain a copy of the transgene in their genome.

Various methods for producing transgenic plants are well known in themselves to those skilled in the art. Generally, these methods involve the transformation of plant cells, the regeneration of plants from the transformed cells, and the selection of the plants having integrated the transgene.

Many techniques for transforming germ-line or somatic plant cells (isolated, in the form of tissue or organ cultures, or on the whole plant) and regenerating the plants are available. The choice of the most appropriate method generally depends on the plant in question.

By way of nonlimiting examples of methods which are usable in the case of the plants mentioned above, it is possible to mention the protocols described by Guis et al. (Scientia Horticulturae 84: 91-99, 2000) for melon, by Hamza and Chupeau (J. Exp. Bot. 44: 1837-1845, 1993) for tomato, by Shoemaker et al. (Plant Cell Rep. 3: 178-181, 1986), by Trolinder and Goodin (Plant Cell Rep. 6: 231-234, 1987) for the cotton plant, by Van der Mark et al. (J. Genet Breeding 44: 263-268, 1990) or by Marchant et al. (Ann. Bot. 81: 109-114, 1998) for rose plants. In the case of monocotyledonous plants, mention may be made, for example of the protocols described by Hiei et al. (The Plant Journal, 6, 271-282, 1994) or Ishida et al. (Nature biotechnology, 14, 745-750, 1996) for corn, or by Rasco-Gaunt et al. (J. Exp. Bot. 52: 865-874, 2001) for wheat.

By way of additional example, the production of *A. thaliana* overexpressing the ZmMYB31 transcription factor has been described by Fornalé et al., 2006 (mentioned above).

A subject of the present invention is also the use of an isolated polynucleotide encoding an R2R3-MYB subfamily 4 transcription factor as defined above, preferably the ZmMYB31 transcription factor of SEQ ID No. 1, for inducing water-stress tolerance in a plant.

The present invention will be understood more clearly by means of the additional description which follows, which refers to nonlimiting examples illustrating the production of transgenic plants overexpressing the R2R3-MYB subfamily 4 transcription factor ZmMYB31 and the demonstration of its role in increasing resistance to water deficit, and also the appended FIG. 1 representing the map of the binary vectors pBIOS1977 (A) and pBIOS1978 (B).

EXAMPLE 1

Production of Transgenic Corns Overexpressing the ZmMYB31 Transcription Factor

1) Cloning and Genetic Transformation of Corn

Two different transformation vectors (pBIOS 1562 and pBIOS 1958) were used for the genetic transformation of the corn. These vectors contain the *Streptomyces hygroscopicus* bar gene conferring resistance to the herbicide bialaphos (White et al., Nucleic Acids Res., 18:1062, 1990), which is of use for selecting the corn transformants, and a gene encoding a GFP (Green Fluorescent Protein) as a visual marker for following the presence of the transgene in the plants and the seeds. The difference between these two vectors lies in the cloning strategy used to introduce the expression cassette containing the gene of interest (cloning via the Gateway® system or restriction cloning) and the promoter for expression of the GFP (the cassava vein mosaic virus (CsVMV) promoter followed by the FAD2 intron of *Arabidopsis* or the endosperm-specific high-molecular-weight glutenin promoter).

According to a first cloning strategy, the synthetic gene encoding ZmMYB31 (SEQ ID No. 5; synthetic sequence optimized for expression in corn) containing the attL1 and attL2 restriction sites was introduced via an LR recombination reaction in the pBIOS 1562 Gateway binary destination vector, thus generating the pBIOS1977 vector (see FIG. 1A). The pBIOS 1562 vector is derived from the pSB12 vector (Komari et al., Plant J., 10:165-174, 1996) containing the bar gene under the control of the pActin promoter, the gene encoding a GFP under the control of the CsVMV promoter followed by the FAD2 intron, and the promoter and the $1^{st}$ intron of rice ubiquitin 3 (Sivamani and Qu, Plant Mol. Biol., 60:225-239, 2006) followed by a Gateway cassette and by a polyadenylation sequence originating from the *Arabidopsis* Sac66 gene (Jenkins et al., Plant Cell Environ., 22:159-167, 1999).

According to a second cloning strategy, the synthetic gene encoding ZmMYB31 (SEQ ID No. 5) was introduced by restriction cloning (presence of SapI restriction sites between the coding region and the attL sites) into the pBIOS 1958 binary destination vector digested with SapI, thus generating the pBIOS1978 vector (see FIG. 1B). pBIOS 1958 is also derived from the pSB12 vector, but has the gene encoding a GFP under the control of the endosperm-specific high-molecular-weight glutenin promoter (HMWG promoter).

The pBIOS1977 or pBIOS1978 vector was then transferred into the *Agrobacterium tumefaciens* strain LBA4404 (pSB1) according to the method described by Komari et al., 1996 (mentioned above).

The corn cultivar A188 was then transformed with this strain of *agrobacterium* containing the pBIOS1977 vector or the pBIOS1978 vector, according to the method described by Ishida et al., 1996 (mentioned above).

The primary transformants (T0) were selected according to routine methods as a function of the following four criteria:
(i) number of copies inserted: this determination was carried out by quantitative PCR. All the transformation events having more than 2 copies of the transgene were eliminated.
(ii) integrity of the T-DNA inserted: this was verified by means of a PCR reaction during the first steps of development of the transformed plant.
(iii) absence of premature termination of the transcription of the transgene: since each of the genes targeted is under the control of a constitutive promoter, it is possible to measure their expression using leaf tissues. The RNA of leaves from T0 plants was therefore extracted and the integrity of the transcripts was verified by RT-PCR using a sense primer located on the rice ubiquitin 3 intron and an antisense primer located on the AtSac66 terminator.
(iv) number of T1 grains harvested.

After selection of the transformants, 52 transgenic lines were obtained, 21 of which have a single and intact transgene.

2) Evaluation of the Tolerance of the Transgenic Plants to Water Deficit

First-generation plants (crossing of the primary transformant with the A188 recurrent line) are evaluated on a phenotyping platform. These transgenic plants are therefore hemizygous for the transgene (dominant trait of the genetic transformation). The controls ("RRS" and "RCP") used in the experiment correspond to the wild-type segregants resulting from this same cross.

2.1 Growing Compartment

The plants studied are cultivated in a phytotron. The latter, with a surface area of 30 m², has two independent growing chambers. In these chambers, the illumination, the temperature and the hygrometry are regulated (see section 2.2 below).

Sowing is carried out in earthenware containers with dimensions of 44×28.5×7 cm (H×W×L). Five genotypes are sown per earthenware container at a rate of ten seeds per genotype. Five plants only per genotype are used to measure the drying out kinetics.

2.2 Growing Conditions

Within the growing compartment, the temperature, the humidity and the illumination are regulated.

The conditions applied are the following:

Photoperiod:
  Day for 16 h (6 am to 10 pm) with photosynthetic supplement (400 W sodium lamp) when the external radiation is less than 100 W/m².
  Night for 8 h (10 pm to 6 am).
Thermoperiod: 24° C./20° C.
  These conditions are adhered to by heating when the temperature is below 20° C. at night or 24° C. during the day, when the temperature exceeds 25° C.
Humidity: 75% relative humidity regulated by nocturnal fogging.
  These various conditions ensure optimum growth of the corn.

2.3 Measurement of Drying Out Kinetics

Relevance of the Trait Measured:

The behavior of the plants with respect to transpiration is studied by means of continuous monitoring of the drop in relative water content (RWC) of small seedlings at a young stage (4 visible leaves). The objective is to study the response in terms of stomatal control of the plants when there is an abrupt interruption of water supply.

A very rapid stomatal control when a water deficit occurs makes it possible to save the available water, but limits the $CO_2$ assimilation capacity and therefore the production potential of the plant. On the other hand, quite late closing of the stomata makes it possible to maintain the photosynthetic activity of the plant ensuring the maintenance of the production potential, with the risk of said plant drying out more rapidly (Khalfaoui, 1991, In: L'amélioration des plantes pour l'adaptation aux milieux arides [Improvement of plants for adaptation to arid environments]. Published by AUPELF-UREF. John Libbey Eurotext, pp. 51-63).

Method:

The measurements are carried out on whole T1 small seedlings at the 3-4 visible leaf stage. The plants used during this measurement are plants resulting from sowing in excess relative to the needs of the platform (3 seeds sown per pot). The numbers for the measurement of drying out are 5 plants per transformation event and wild-type controls.

The plants were cut at the neck, submerged for 24 hours at 4° C. in the dark (in order to saturate the cells with water) and then placed in a luminous climatic chamber regulated at 30° C.

The weight of the small seedlings is then monitored according to the timetable detailed in table II below:

TABLE II

Timetable of the weighing of small seedlings conditioned at 30° C. in full light. The weight at H0 corresponds to the weight at full turgidity. At the end of day 3, the small seedlings are placed in an incubator at 80° C. for 24 h in order to obtain, by means of a final weighing, the dry weight value.

| Day | Duration | | |
|-----|----------|---|---|
| 1 | H0 | ← | Weight full turgidity ($W_{Turg}$) |
| 1 | H0 + 2 | | |
| 1 | H0 + 6 | ← | Weight at time t ($W_t$) |
| 1 | H0 + 8 | | |
| 4 | H0 + 96 | ← | Dry weight ($W_d$) |

At time t, the relative water content of the plants is then calculated according to the following mathematical formula: $(W_t - W_d)/(W_{Turg} - W_d) \times 100$.

The invention claimed is:

1. A method of increasing the tolerance of a corn plant to water deficit, comprising overexpressing in said corn plant a R2R3-MYB subfamily 4 transcription factor, having at least 95% identity with the sequence SEQ ID NO: 1, wherein said R2R3-MYB subfamily 4 transcription factor is derived from a monocotyledonous plant, and comprises the conserved amino acids located at positions 1-9, 11-13, 15-22, 24-25, 27, 30-41, 43-70, 74-75, 77-78, 80-83, 85-93, 95-111, 113-116, 120-127, 138, 140-141, 197, 202-212, 214, 234, 239, 242, 252, 254-255, 261-263, 267-271 and 274-275 of said sequence SEQ ID NO: 1 when it is aligned with said sequence SEQ ID NO: 1 and said overexpression is obtained by:
   genetic transformation of said corn plant with one or more copies of a polynucleotide encoding said R2R3-MYB subfamily 4 transcription factor, combined with cis regulatory sequences for its expression.

2. The method as claimed in claim 1, wherein said R2R3-MYB subfamily 4 transcription factor has the sequence set forth in SEQ ID NO: 1.

3. The method as claimed in claim 1, wherein the R2R3-MYB subfamily 4 transcription factor has at least 98% identity with the sequence SEQ ID NO: 1.

4. The method as claimed in claim 1, wherein said R2R3-MYB subfamily 4 transcription factor is derived from a corn plant.

5. The method as claimed in claim 1, wherein the corn plant is transformed with a recombinant expression cassette comprising a polynucleotide encoding the R2R3-MYB subfamily 4 transcription factor as defined in claim 1, placed under the transcriptional control of a promoter.

6. The method as claimed in claim 5, wherein the promoter is a heterologous promoter.

7. The method as claimed in claim 6, wherein the heterologous promoter is a constitutive promoter.

8. The method as claimed in claim 7, wherein the constitutive promoter is the rice ubiquitin 3 promoter.

* * * * *